United States Patent [19]

Stille et al.

[11] Patent Number: 5,374,427
[45] Date of Patent: Dec. 20, 1994

[54] IMPLANTABLE ACTIVE SUBSTANCE DEPOT MATERIAL

[75] Inventors: Wolfgang Stille; Gabriele Gentschew, both of Frankfurt am Main; Peter Reitz, Obertshausen; Thomas Erben, Wiesbaden; Werner Zöllner, Oberpfaffenhofen; Klaus-Peter Stefan, Seefeld, all of Germany

[73] Assignee: Thera Patent GmbH & Co. KG, Seefeld, Germany

[21] Appl. No.: 989,460

[22] Filed: Dec. 10, 1992

Related U.S. Application Data

[63] Continuation of Ser. No. 717,326, Jun. 18, 1991, abandoned.

[30] Foreign Application Priority Data

Jun. 20, 1990 [DE] Germany ............... 4019617

[51] Int. Cl.$^5$ .............. A61F 2/28; A61K 31/74; A61K 6/08; A01N 25/08
[52] U.S. Cl. .............. 424/423; 424/425; 424/426; 424/409; 523/115; 523/116
[58] Field of Search ......... 424/77, 78.08, 81, 405, 424/409, 422, 423, 425, 484, 486, 487, 674, 684, 426, 78.37; 514/724, 772.3; 521/97; 523/115, 116; 524/2, 5

[56] References Cited

U.S. PATENT DOCUMENTS

| | | | |
|---|---|---|---|
| 3,814,717 | 6/1974 | Wilson et al. | 433/228.1 |
| 3,986,998 | 10/1976 | Schmitt et al. | 523/116 |
| 4,016,124 | 4/1977 | Crisp et al. | 523/116 |
| 4,059,684 | 11/1977 | Gross et al. | 424/423 |
| 4,137,086 | 1/1979 | Potter et al. | 501/73 |
| 4,143,018 | 3/1979 | Grisp et al. | 524/559 |
| 4,191,740 | 3/1980 | Heusser et al. | 424/489 |
| 4,233,287 | 11/1980 | Heusser et al. | 424/489 |
| 4,360,605 | 11/1982 | Schmitt et al. | 523/116 |
| 4,376,835 | 3/1983 | Schmitt et al. | 523/116 |
| 4,674,661 | 6/1987 | Herold | 222/386 |
| 4,797,282 | 1/1989 | Wahlig et al. | 424/423 |
| 4,814,362 | 3/1989 | Billington et al. | 523/117 |
| 4,853,225 | 8/1989 | Wahlig et al. | 424/423 |
| 4,927,866 | 5/1990 | Purrmann et al. | 523/116 |

FOREIGN PATENT DOCUMENTS

| | | |
|---|---|---|
| 531850 | 2/1981 | Australia . |
| 0357327 | 7/1990 | European Pat. Off. . |
| 2065824 | 3/1976 | Germany . |
| 2319716 | 7/1976 | Germany . |
| 2621003 | 12/1976 | Germany . |
| 2560153 | 10/1979 | Germany . |
| 3510234 | 10/1985 | Germany . |
| 1316129 | 5/1973 | United Kingdom . |
| 1532954 | 11/1978 | United Kingdom . |
| 1532955 | 11/1978 | United Kingdom . |
| 2190372 | 11/1987 | United Kingdom . |

OTHER PUBLICATIONS

Abstract FR2610916A (English language).
Abstract EP 340016A (English language).
Abstract EP 228592 (English language).
Abstract EP 301759A (English language).
Abstract EP 219058A (English language).
Abstract GB 1554555.
Abstract DE 2759602 (English language).
Abstract DE 3634697 (English language).
Abstract DE 3000118A (English language).
Abstract DE 2750326A (English language).
Abstract DE 2547744A (English language).
Abstract DE 2319715A (English language).
Abstract for DE 2727535-A (English language).
Jonck et al, Clinical Materials, vol. 4, pp. 85–107 (1989).

Primary Examiner—Thurman K. Page
Assistant Examiner—C. Azpuru
Attorney, Agent, or Firm—Birch, Stewart, Kolasch & Birch

[57] ABSTRACT

An implantable active substance depot material which contains a glass ionomer cement and one or more chemotherapeutic agents. The active substance depot materials ensure an initially high release rate of the active substance therein and subsequently a discharge of the active substance in small doses until complete depletion of the deposited active substance has occurred.

21 Claims, No Drawings

IMPLANTABLE ACTIVE SUBSTANCE DEPOT MATERIAL

This application is a continuation of application Ser. No. 07/717,326 filed on Jun. 18, 1991, now abandoned.

FIELD OF THE INVENTION

The present invention provides materials which are especially suited to form implantable active substances depots.

BACKGROUND OF THE INVENTION

With increasing frequency, systemic therapies are being replaced by local ones, since in this way high levels of active substances can be attained in regions of the body which are difficult to reach, without the necessity of applying or administering high, often toxic, chemotherapeutic doses over the whole body.

DE-C-20 22 117, 25 11 122 and 27 27 535 describe bone cements based on polymethyl methacrylate (PMMA) which contain an antibiotic such as gentamycin. Additionally, other antibiotic-containing bone cements based on PMMA are known. Thus, for example, EP-A-O 301 759 describes PMMA bone cements which contain erythromycin and DE-A-35 42 972 and 35 43 164 describe PMMA bone cements which contain so-called gyrase inhibitors. It is also known to use implants based on the aforementioned PMMA bone cements in a pre-finished form for local antibiotic therapy, reference being drawn, for example, to DE-C-26 51 441 and 27 27 535.

The release of gyrase inhibitors from ceramic carrier materials such as tricalcium phosphate is also described, for example, in DE-A-35 42 972.

Furthermore, it is known to add cytostatics, for example methotrexate, to "bone cements" based on PMMA (see e.g., H. Wahlig, E. Dingeldein in "Primär- und Revisionsalloarthroplastik", published by Endo-Klinik, Hamburg, Springer-Verlag, Berlin 1987, page 357).

Since the early 70's glass ionomer cements have been used in dental medicine as filling materials and also for securing crowns and bridges (e.g., DE-A-20 61 513). In such processes the materials harden by reaction of the basic glass powder with a polymeric polyacids which is accompanied by the formation of a highly polar calcium-aluminum polysalt matrix. The use of glass ionomer cements in bone cement is likewise knowns (see e.g., L. M. Jonck, C. J. Grobbelaar, H. Strating, Clin. Mat. 4. 85 (1989)). Finally, it is known to use glass ionomer cements in a porous form as bone replacement materials (see e.g., DE-A-38 06 448).

The use of PMMA bone cements as active substance depots produces various disadvantages. For example, the materials still contain even in their hardened forms, perceptible amounts of health-damaging monomers, particularly methyl methacrylate, as well as unreacted peroxides and other radical formers. Moreover, when unhardened material is inserted for cementing purposes, a setting temperature of up to 80° C. is reached during setting, which can destroy adjacent body tissue. Furthermore, the release of active substance from such bone cements (and the implants produced therefrom) is satisfactory in only a very few selected cases. For example, it is desirable to have depots provide an initially high release, followed by a subsequent continuous release of smaller doses within 2 to 30 days; in ideal situations, after this period, no more active substance should be discharged. With active substance depots based on PMMA, this could hitherto not be satisfactorily achieved.

SUMMARY OF THE INVENTION

The present invention avoids the aforementioned disadvantages of the prior art and provides active substance depots which allow for an optimum discharge of an active substance therefrom. Surprisingly, it has been found that the use of glass ionomer cements and chemotherapeutics, such as antibiotics and cytostatics, provide an ideal depot combination. With the depots and implants of the present invention, high initial release rates can be attained with compounds (for example, with antibiotics, such as clindamycin), which otherwise do not release satisfactory from PMMA depots and implants. Likewise, the depots and implants of the present invention allow the active substances therein to be subsequently discharged in small amounts over long time periods until virtually no more active substances are left to be discharged. This is particularly advantageous and totally unexpected, since active polar substances such as clindamycin, are usually not released from extremely polar matrixes. As such, it was expected heretofore that such active substances would be retained in a glass ionomer cement matrix and not be released therefrom.

More particularly, the present invention provides an implantable depot material comprising a glass ionomer cement and one or more chemotherapeutically active compounds. The depots according to the invention preferably comprise the following constituents:

(a) an aluminum fluorosilicate glass,
(b) at least one polyacid with an average molecular weight of $>500$,
(c) optionally water,
(d) a chemotherapeutically active substance,
(e) optionally a carbonate and/or hydrogen carbonate in a quantity of at least 0.1% by weight based on the amount of (a) present, or another foam-generating agent and
(f) optionally a chelating agent.

DETAILED DESCRIPTION OF THE INVENTION

In a preferred embodiment of the present invention, the depot materials comprise a liquid part containing from 40 to 90% by weight of water, from 10 to 60% by weight of polyacid and from 0 to 20% by weight of a chelating agent, and a solid part containing from 80 to 99.89% by weight of aluminum fluorosilicate glass, from 0.01 to 3% by weight of one or more chemotherapeutics and optionally from 0.1 to 20% by weight of a carbonate and/or hydrogen carbonate.

In a further embodiment, the depot materials according to the present invention comprise a liquid part containing from 80 to 100% by weight of water and from 0 to 20% by weight of a chelating agent, and a solid part comprising from 5.0 to 94.89% by weight of aluminum fluorosilicate glass, from 5.0 to 49.98% by weight of dry polyacid, from 0.01 to 3% by weight of one or more chemotherapeutics and optionally from 0.1 to 20% by weight of a carbonate and/or hydrogen carbonate.

Additionally, stabilizers, preservatives, such as e.g., benzoic acid, thixotropy auxiliaries, disinfectants, pigments, X-ray contrast agents and further fillers can also be incorporated into the depot materials of the present invention.

The active substance depot materials according to the invention may be used in a plastic form for cementing purposes, but they are preferably set in the form of pre-finished molded parts, in particular in the shape of granules with foam molded parts being preferred.

When the depot materials are used in a plastic form, the chemotherapeutic active agents are added to the other components of the depot materials. An appropriate form can comprise pre-mixed individual constituents, if so desired. For example, the six constituents (a)–(f), as mentioned above, can for example be distributed as follows between two components A and B.

|   | A | B |
|---|---|---|
| 1 | a + b + d | c |
| 2 | a + b | c + d |
| 3 | a + d | b + c |
| 4 | a | b + c + d |

The chelating agent (f) can be added to either of the components A or B, while the foaming agent (e) is preferably found in the component which does not contain any acid (b) or (f) (this limitation does not apply to dry compositions).

If, when processing the material according to the present invention, the solid and liquid parts are mixed together, the reaction of the polyacid with the aluminum fluorosilicate glass gives rise to a molded part which, due to the simultaneous reaction of the polyacid with the carbonate and/or hydrogen carbonate, is provided with interconnecting macropores.

The chemotherapeutic active agent can be incorporated into the molded parts, for example, in the plastic phase as described above, or through impregnation of previously manufactured molded parts of the glass ionomer cement, preferably foamed molded parts. The parts are impregnated with the chemotherapeutic active agent in a suitable solvent which should by physiologically acceptable. The solvent can thereafter be removed in a usual manner, as known by those skilled in the art, before implantation of the molded parts. The molded parts which are formed preferably have a granular or a spherical form and a maximum particle size of <20 mm, preferably of <5 mm. Especially preferred are granulates with the particle sizes of about 0.5–1 mm, about 1–2 mm, about 2–3 mm and about 3–4 mm. The molded parts can be used individually and also as chains (in an amount analogous to the known PMMA chains from DE-C-26 51 441) as active substance depots. A combination of active substance depots based on glass ionomer cement and on PMMA is also encompassed hereby for special indications, if so desired.

Possible areas of indication for the compositions prepared according to the present invention are, e.g., antibiotic-containing cements for securing artificial joints (e.g., knees, hips), for reconstruction of bone defects, for producing retrograde root fillings in connection with a root tip resection, for cementing an apical titanium or gold pin in connection with a root tip resection, for cementing a gutta-percha pin in connection with an orthograde root filling or for pulpitis treatment as dental filling material.

Cytostatic-containing cements can, for example, be used to fill bone cavities after surgical tumor removals.

Antibiotic-containing molded parts or granules can be used for reconstruction of bone defects, e.g., in the cranium area, for filling infected mastoid cavities, for filling large defects in the case of acetabulum revisions and in connection with preservative dentistry, as a constituent of a base-filling for treatment of acute caries or as a molded part or chain in the case of bone and/or soft part infections, possibly in connection with the already known PMMA chains.

Cytostatic-containing molded parts or granules can advantageously be used for reconstruction and/or filling of bone defects after surgical or cryosurgical tumor removal.

The combination of pre-finished molded parts and plastically incorporated cement can also be useful. Depending upon the medical indication presented, the molded parts and cements for this can contain identical or different active substances and/or active substance combinations.

The porous molded parts which can be prepared with the materials according to the present invention, can be lightly ground at the surface before being used, so that the resultant pores therein are freely accessible.

With the materials according to the present invention, the advantages of readily bio-compatible materials, such as hydroxy apatite ceramics, can be combined with the ready applicability of filled polyacrylates without having to accept disadvantages such as the addition of resorbable substances, use of strong acids, use of toxicologically objectionable monomers and the difficulties accompanying the shaping of hard ceramics and glasses.

With the materials according to the present invention, paste-like compositions can be admixed for bone replacement use, which can be molded by the surgeon, simply and without the use of machining tools, into the desired shape during the operation; or they may be directly filled into bone defects, with hardening then taking place in the bone. Readily compatible bone replacement parts are obtained within which bone material can readily grow (due to the parts' porosity) and which, with setting, do not damage the surrounding bone material by acid attack or steep temperature rises.

The macroporosity of the molded parts can be influenced by the particle size and quantity of the carbonates and/or hydrogen carbonates used, and by the solubility of the carbonates chosen and of the polyacid used. Ideally, bone replacement parts can be produced which in terms of porosity equal the surrounding bone material, particularly the spongiosa.

The individual components of the materials according to the present invention can be used in predosed amounts in administration devices (e.g., capsules), as described in DE-A-34 07 648. In these administration devices, the powdery solid component is generally located in the capsule interior, while the liquid component is located in a sachet at the capsule wall. Before application, the contents of the sachet liquid are pressed with a special activator through a hole in the capsule wall into the capsule interior. By shaking, the contents are homogeneously mixed. The material can then be brought directly out of the capsule into the bone opening. With this application method, it is advantageous if glass and carbonate and/or hydrogen carbonate are stored in the capsule interior as powder, and the polyacid and the optional chelating agent as liquid components in the sachet.

The calcium aluminum fluorosilicate glasses described in DE-A-20 61 513 and EP-A-0 023 013 and the strontium aluminum fluorosilicate glasses described in EP-A-0 241 277 can be used as constituent (a) of the depot materials. In addition to oxygen, the aluminum fluorosilicate glasses used according to the present invention preferably comprise:

| Constituent | Calculated as | % by weight |
|---|---|---|
| Si | $SiO_2$ | 20–60 |
| Al | $Al_2O_3$ | 10–50 |
| Ca | CaO | 0–40 |
| Sr | SrO | 0–40 |
| F | F | 1–40 |
| Na | $Na_2O$ | 0–10 |
| P | $P_2O_5$ | 0–10 | where at least 1% by weight of CaO and/or SrO must be present and overall from 0 to 20% by weight, calculated as oxides, of B, Bi, Zn, Mg, Sn, Ti, Zr, La (or other trivalent lanthanoids, K, W, Ge) and other additives, which do not impair the characteristics and are physiologically unobjectionable. By adding from 10 to 20% by weight of $La_2O_3$, the glasses can be made X-ray-visible.

The powder particles advantageously comprise:
Si as $SiO_2$ 25–50% by weight
Al as $Al_2O_3$ 10–40% by weight
Ca as CaO 0–35% by weight
Sr as SrO 0–35% by weight
F 5–30% by weight
Na as $Na_2O$ 0–8% by weight
P as $P_2O_5$ 1–10% by weight
where at least 10% by weight of Ca (calculated as CaO) and/or Sr (calculated as SrO) must be present and 0–10% by weight of $B_2O_3$, $Bi_2O_3$, ZnO, MgO, $SnO_2$, $TiO_2$, $ZrO_2$, $La_2O_3$ (or other oxides of trivalent lanthanoids, $K_2O$, $WO_3$, $GEO_2$) and other additives, which do not impair the characteristics and are physiologically unobjectionable.

It is especially preferred to use powders which comprise:
Si as $SiO_2$ 25–45% by weight
Al as $Al_2O_3$ 20–40% by weight
Ca as CaO 10–30% by weight
F 10–30% by weight
Na as $Na_2O$ 1–8% by weight
P as $P_2O_5$ 1–10% by weight The glass powders used according to the present invention have an average particle size (weight average) of at least 1 μm and preferably at least 3 μm. Preferably, the average particle size (weight average) is 1–20 μm, more preferably 3–15 μm and most preferably 3–10 μm. The particles have a maximum particle size of 150 μm, preferably 100 μm, most preferably 60 μm.

The powders thus obtained are optionally subjected to a surface treatment according to European Patent 0 023 013. In this process, the glass powders are treated on their surfaces with acid, preferably at room temperature. Here, substances containing acid groups are used, e.g, hydrochloric acid, sulfuric acid, nitric acid, acetic acid, propionic acid or perchloric acid, which acids form soluble calcium salts or strontium salts. The acids are used in a concentration of from 0.01 to 10% by weight, preferably from 0.05 to 3% by weight. After the corresponding reaction time, the powders are separated from the solution and thoroughly washed out, so that practically no soluble calcium or strontium salts remain on the surface of the powder particles.

The polyacids used as constituent (b) can also be the polycarboxylic acids known to be used in the preparation of glass ionomer cement powders, e.g., polymaleic acid, polyacrylic acid, polyitaconic acid and mixture(s) of these or copolymers of these (in particular the maleic acid-acrylic acid copolymers and/or acrylic acid-itaconic acid copolymers known from EP-B-O 024 056). The average molecular weight of the polycarboxylic acids used in the present invention is more than 500. Advantageously, the polycarboxylic acids have a molecular weight of 1,000 to 20,000, especially preferred are those with average molecular weights of 3,000 to 10,000. The polycarboxylic acid is preferably used in a concentration of 5 to 50% by weight, relative to the amount of constituent (a), which is present.

Polyphosphonic acids, (e.g., polyvinyl phosphonic acid) are also suitable as the polyacido These polyphosphonic acids can completely or partly replace the aforementioned polycarboxylic acids in the depot materials.

In order to obtain high storage stabilities of the bone replacement materials prior to application, the addition of preservatives is recommended, e.g., benzoic acid, in particular to the dry polyacid component.

As constituent (f), a chelating agent, such as described in DE-A-23 19 715, can be utilized. Preferably, tartaric acid is used as chelating agent.

As a foam-forming constituent (e), all carbonates and/or hydrogen carbonates are suitable; these are preferably at least partly soluble in the aqueous polyacid solution, which optionally also contains chelating agents. Physiologically compatible carbonates, such as the carbonates and/or hydrogen carbonates of the alkali and/or alkaline earth metals are preferably used. Especially preferred are the carbonates and hydrogen carbonates of magnesium, calcium and strontium.

The carbonates and/or hydrogen carbonates usable as foam-forming constituent (e) are preferably used in concentrations of from 0.1 to 20% by weight in relation to constituent (a); from 0.5 to 5% by weight are preferably used and from 1 to 3% by weight are most preferably used.

In addition, other foaming agents can also be used, reference being drawn to the entire contents of DE-A-39 27 984.

As foaming agents (e), all materials which can cause foaming in the production of the molded parts are suitable. Thus, with the liquid constituents ($H_2O$ or $H_2O$ acid), with added surfactants and/or emulsifiers and stirring in gases (e.g., air), it is possible to produce stable foams to which the other constituents (e.g., glass) can then be added (see e.g., Ullmanns Enzyklopadie der technischen Chemie, Volume 22, page 463, Verlag Chemie, 4th Edition, 1982). Also suitable are metal hydrides, in particular, sodium boron hydride, which cause a foaming of the hardening cement with protons (water or acids), accompanied by hydrogen development.

A further possibility for foam formation is to use an aqueous solution of a gas, e.g., $CO_2$ or $SO_2$, which is expelled by the added acid when the cement is produced and thus causes foaming.

It is also possible to add peroxides, e.g., $H_2O_2$, which lead to foaming either through the effect of acid and/or through metal catalysis accompanied by decomposition and oxygen release. Thus, it is for example also possible to use an aqueous $H_2O_2$ solution for mixing the cement and to incorporate a corresponding amount of $FeSO_4$ into the powder, which upon the bringing together of the two components, causes oxygen development and thus foaming.

Additionally, the foaming agents may be propellants, such as solid organic propellants (e.g., azodicarbonamide, azobis-(isobutyronitrile), diphenyl oxide-disulphonic acid hydrazide and N-nitroso-compounds), solid inorganic propellants, liquid propellants (e.g., hydrocarbons and halogenated hydrocarbons) and gaseous propellants (e.g., $N_2$, $CO_2$ and air).

The solid and liquid foaming agents are usually used in a concentration of 0.1 to 50% by weight, based on the total mixture, especially preferably 0.1 to 20% by weight, the gaseous foaming agents are used in quantities of 5 to 90% by volume, based on the total mixture, preferably 10 to 60% by volume.

The weight ratio of constituent (b) to constituent (e) is preferably at least 3:1, especially preferred is a weight ratio of at least 10:1.

The carbonates and/or hydrogen carbonates preferably have an average particle size of 0.1 to 200 μm, preferably of 1 to 100 μm, most preferably of 5 to 50 μm.

The solubility of the carbonates and/or hydrogen carbonates can be regulated by the choice of the cation(s). They should be dimensioned in such a way that the foaming process continues until setting commences. When rapid setting is desired, the choice of easily soluble alkali carbonates and/or hydrogen carbonates is thus recommended, and for slow setting, the choice of low-solubility carbonates and/or hydrogen carbonates is recommended.

As the chemotherapeutic agent (d), those active agents which are suitable for the present invention are, for example, cytostatics, in particular methotrexate, vincristine, cisplatin, cyclophosphamide or an antibiotic, in particular a gyrase inhibitor, such as for example, ciprofloxacin, ofloxacin, norfloxacin and salts thereof as well as aminoglycoside antibiotics, in particular the class of lincomycins. Most preferred are clindamycin and lincomycin and salts and derivatives thereof. The combination of several active substances can also be suitable to optimally supply special areas of indication. With regard to suitable gyrase inhibitors encompassed hereby, reference is made to W. Stille, FAC volume 6–10, 1987, pages 1575–1583. All gyrase inhibitors described therein are encompassed herein.

The concentration of the chemotherapeutic agent is a maximum of 10% by weight, preferably a maximum of 3% by weight based on the total weight of the active substance depot material. Especially preferred is a range from 0.01 to 3% by weight. With higher doses, the mechanical properties of the glass ionomer cement, or of the implants produced therefrom, are impaired.

EXAMPLES

In all Examples, a calcium aluminum fluorosilicate glass powder with the oxide composition as set out in Table 1 is used.

TABLE 1

| Si as $SiO_2$ | 33.8 parts by weight |
|---|---|
| Al as $Al_2O_3$ | 28.3 parts by weight |
| Ca as CaO | 14.4 parts by weight |
| Na as $Na_2O$ | 2.6 parts by weight |
| P as $P_2O_5$ | 6.7 parts by weight |
| F | 17.3 parts by weight |

Example 1

100 parts by weight of the glass powder as per Table 1 are homogeneously mixed with 1.1 parts by weight of clindamycin hydrochloride (corresponding to 0.97 parts clindamycin) to form a powder mixture I.

50 parts by weight of $H_2O$, 40 parts by weight of a copolymer comprising acrylic acid and maleic acid (1:1, average molecular weight 7000), 9.1 parts by weight tartaric acid and 0.9 parts by weight benzoic acid are stirred to form a homogeneous solution I.

2.6 parts by weight of the powder mixture I and 1 part by weight of the solution I are mixed to homogeneous state within half a minute. The material had a processing time of four minutes, and in this time cylindrical molded parts with a diameter of 0.6 cm and a height of 1.2 cm were produced. 20 minutes after their production, the parts were introduced into 5 m phosphate buffer of pH 7.4 at 37° C. and eluted. At given times, the total elution solution was changed. The antibiotics content of the eluate was determined in an agar-diffusion test bio-assay (see Table 2). The indicator seed which was used for clindamycin was S. aureus ATCC 25923. Non medicated test specimens made of glassy ionomer cement (without the addition of clindamycin) showed no inhibition areas.

TABLE 2

| Release of clindamycin from glass ionomer cement | |
|---|---|
| Removal time in days | Amount released in μg |
| 1 | 200 |
| 3 | 82 |
| 6 | 80 |
| 14 | 78 |
| 28 | 74 |
| 35 | 20 |

The recovery rate after 35 days was approximately 12% (accumulated absolute release amount).

The material is outstandingly suitable for use as a bone cement. It corresponds very well to bone substance and has good adhesive properties to bone. The compressive strength of the cement is 123 MPa, its flexural strength is 20 MPa.

Example 2

100 parts by weight of the glass recited in Table 1, 2.5 parts by weight of clindamycin hydrochloride (corresponding to 2.2 parts pure clindamycin) and 2 parts by weight of calcium carbonate (Merck, average particle size <40 μm) were worked together to produce a homogeneous powder mixture II.

35 parts by weight of the polycarboxylic acid mentioned in Example 1, 0.9 parts by weight of benzoic acid and 64.1 parts by weight of distilled water were worked together to produce a homogeneous solution II.

2 parts by weight of the powder mixture II and 1 part by weight of the solution II were homogeneous mixed together within half a minute.

Through the addition of calcium carbonate, the material foams and produces an open-pored foamed cement, which can also be worked into granules. The material is outstandingly suitable for the filling of bone defects and for the cementing of non-pressurized implants.

As described in Example 1, cylindrical molded parts were produced and then test specimens were eluted in phosphate buffer of pH 7.4 and their antibiotic content was measured by means of bio-assay at the times listed in Table 3.

TABLE 3

| Release of clindamycin from foamed glassy ionomer cements | |
|---|---|
| Removal time in days | Amount released in μg |
| 1 | 1800 |
| 2 | 120 |
| 7 | 190 |

TABLE 3-continued

| Release of clindamycin from foamed glassy ionomer cements | |
|---|---|
| Removal time in days | Amount released in µg |
| 14 | 40 |
| 28 | 25 |
| 35 | <10 |

The overall recovery rate is 72%. The material as outstandingly suitable for forming an active substance depot. It releases a large amount of the active substance within the first 24 hours and within the following weeks also ensures a continuous further discharge in small doses, until finally no more measurable antibiotics content is discharged.

The invention being thus described, it will be obvious that the same may be varied in many ways. Such variations are not to be regarded as a departure from the spirit and scope of the invention, and all such modifications as would be obvious to one skilled in the art are encompassed within the scope of the following claims.

What is claimed is:

1. An implantable active substance depot material, comprising:
   (a) an aluminum fluorosilicate glass,
   (b) at least one polyacid with an average molecular weight of >500, and
   (c) a chemotherapeutic agent selected from the group consisting of a cytostatic and an antibiotic.

2. An implantable depot material as recited in claim 1, the depot material further comprising:
   (d) water.

3. An implant depot material as recited in claim 1, the depot material further comprising
   (d) water, and
   (e) a foam forming agent.

4. An implantable material as recited in claim 1, the depot material further comprising:
   (d) water, and
   (e) a carbonate, hydrogen carbonate or a mixture thereof in a quantity of at least 0.1% by weight based on the amount of component (A) which is present.

5. An implantable depot material as recited in claim 1, the depot material further comprising:
   (d) water,
   (e) a foam forming agent, and
   (f) a chelating agent.

6. An implantable depot material as recited in claim 1, the depot material further comprising:
   (d) water,
   (e) a carbonate, hydrogen carbonate or a mixture thereof in a quantity of at least 0.1% by weight based on the amount of component (A) which is present, and
   (f) a chelating agent.

7. An implantable depot material as recited in claim 1, wherein the chemotherapeutic agent is an antibiotic selected from the group consisting of a gyrase inhibitor, a lincomycin and clindamycin.

8. An implantable depot material as recited in claim 1, wherein the chemotherapeutic agent is a cytostatic selected from the group consisting of methotrexate, vincristine, cisplatin and cyclophosphamide.

9. An implantable depot material as recited in claim 5, wherein the chemotherapeutic agent is an antibiotic selected from the group consisting of a gyrase inhibitor, a lincomycin and clindamycin.

10. An implantable depot material as recited in claim 5, wherein the chemotherapeutic agent is a cytostatic selected from the group consisting of methotrexate, vincristine, cisplatin and cyclophosphamide.

11. A molded form, which is prepared by hardening a depot material as recited in claim 1.

12. A molded form, which is prepared by hardening a depot material as recited in claim 5.

13. A process for the preparation of an active substance depot material, the process comprising the step of incorporating one or more chemotherapeutic agents selected from the group consisting of a cytostatic and an antibiotic, in a glass ionomer cement comprising the following ingredients:
   (a) an aluminum fluorosilicate glass, and
   (b) at least one polyacid with an average molecular weight of >500.

14. A process as recited in claim 13, wherein the glass ionomer cement further comprises:
   (c) water.

15. A process as recited in claim 13, wherein the glass ionomer cement further comprises:
   (c) water, and
   (d) a foam forming agent.

16. A process as recited in claim 13, wherein the glass ionomer cement further comprises:
   (c) water,
   (d) a foam forming agent, and
   (e) a chelating agent.

17. A process as recited in claim 13, wherein the glass ionomer cement further comprises:
   (c) water, and
   (d) a carbonate, hydrogen carbonate or a mixture thereof in a quantity of at least 0.1% by weight based on the amount of component (a) which is present.

18. A process as recited in claim 13, wherein the glass ionomer cement further comprises:
   (c) water,
   (d) carbonate, hydrogen carbonate or a mixture thereof in a quantity of at least 0.1% by weight based on the amount of component (a) which is present, and
   (e) a chelating agent.

19. An implantable depot material as recited in claim 1, wherein the chemotherapeutic agent is cis-platinum.

20. A molded form which is prepared by hardening a depot material as recited in claim 19.

21. A process for the preparation of an active substance depot material as recited in claim 13, wherein the chemotherapeutic agent cisplatinum is incorporated in said glass ionomer cement.

* * * * *